(12) United States Patent
Castelli et al.

(10) Patent No.: US 11,116,516 B2
(45) Date of Patent: Sep. 14, 2021

(54) DISTAL RADIAL COMPRESSION DEVICE

(71) Applicant: Medtronic Vascular, Inc., Santa Rosa, CA (US)

(72) Inventors: Brian Castelli, Rohnert Park, CA (US); Mary Christopher, San Francisco, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 230 days.

(21) Appl. No.: 16/529,326

(22) Filed: Aug. 1, 2019

(65) Prior Publication Data
US 2020/0038036 A1    Feb. 6, 2020

Related U.S. Application Data

(60) Provisional application No. 62/714,865, filed on Aug. 6, 2018.

(51) Int. Cl.
| *A61B 17/135* | (2006.01) |
|---|---|
| *A61B 17/00* | (2006.01) |
| *A61B 17/12* | (2006.01) |

(52) U.S. Cl.
CPC .. *A61B 17/135* (2013.01); *A61B 2017/00557* (2013.01); *A61B 2017/00907* (2013.01);
(Continued)

(58) Field of Classification Search
CPC ........ A61B 2017/12004; A61B 17/132; A61B 17/1322; A61B 17/1325; A61B 17/1327;
(Continued)

(56) References Cited

U.S. PATENT DOCUMENTS 4,294,237 A * 10/1981 Frazier ................ A61F 5/05866
602/21
4,633,863 A    1/1987 Filips et al.
(Continued)

FOREIGN PATENT DOCUMENTS

| CN | 205814373 U | 12/2016 |
|---|---|---|
| GB | 2486194 A1 | 6/2012 |

(Continued)

OTHER PUBLICATIONS

Zhou et al, "Transient ulnar artery compression facilitates transradial access", Medicine, Dec. 2, 2016, 4 pp.
(Continued)

*Primary Examiner* — Wade Miles
*Assistant Examiner* — Kankindi Rwego
(74) *Attorney, Agent, or Firm* — Shumaker & Sieffert, P.A.

(57) ABSTRACT

In some examples, a tissue compression device configured to apply pressure at the snuffbox includes a flexible backing adjustably mechanically connected to a base, and an expandable member mechanically connected to the flexible backing. The base includes a major surface configured to engage a palmar surface of a hand of a patient, for example, to position the hand of the patient in a predetermined configuration, and a plurality of base attachment structures extending from the major surface. The flexible backing is adjustably mechanically connected to the base via the plurality of base attachment structures. The expandable member is configured to be positioned over the snuffbox of the hand of the patient and apply pressure to tissue at the snuffbox when the palmar surface of the hand is engaged with the major surface of the base.

23 Claims, 7 Drawing Sheets

(52) U.S. Cl.
CPC .............. *A61B 2017/00955* (2013.01); *A61B 2017/12004* (2013.01)

(58) Field of Classification Search
CPC .............. A61B 17/135; A61B 17/1355; A61B 2017/00557; A61B 2017/00907; A61B 2017/00955; A61F 5/012; A61F 5/05866; A61F 5/013; A61F 5/01; A61F 5/0118; A61F 5/05816; A61F 5/05875; A61F 5/30; A61F 2007/0001; A61F 2007/0029; A61F 2007/0036; A61F 2007/0037; A61F 2007/0038
USPC .................................. 606/201, 202, 203, 204
See application file for complete search history.

(56) References Cited

U.S. PATENT DOCUMENTS

| | | | |
|---|---|---|---|
| 5,279,545 A * | 1/1994 | Reese, Sr. ............... | A61F 5/013 602/21 |
| 5,413,553 A * | 5/1995 | Downes ................. | A61F 5/0118 2/159 |
| 5,652,955 A * | 8/1997 | Skewis ................. | A41D 13/088 2/16 |
| 6,146,347 A * | 11/2000 | Porrata ................. | A61F 5/0118 128/879 |
| 6,217,536 B1 * | 4/2001 | Gustafson ................. | A61F 5/32 128/879 |
| 6,827,727 B2 | 12/2004 | Stålemark et al. | |
| 6,986,779 B2 * | 1/2006 | Begley ................... | A61H 39/04 601/148 |
| 8,652,080 B2 | 2/2014 | Benz et al. | |
| 9,408,611 B1 | 8/2016 | Pancholy et al. | |
| 9,427,239 B2 | 8/2016 | Benz et al. | |
| 9,463,026 B2 | 10/2016 | Corrigan, Jr. | |
| 9,763,670 B2 * | 9/2017 | Atthoff ............... | A61B 17/1325 |
| 9,867,625 B2 | 1/2018 | Finkielsztein et al. | |
| 10,092,297 B2 | 10/2018 | Hoff et al. | |
| 10,357,254 B2 | 7/2019 | Pancholy et al. | |
| 2012/0238934 A1 | 9/2012 | Düring | |
| 2015/0305751 A1 | 10/2015 | Hoff et al. | |
| 2016/0174952 A1 | 6/2016 | Shah | |
| 2016/0206298 A1 | 7/2016 | Keene et al. | |
| 2016/0213373 A1 | 7/2016 | Drasler et al. | |
| 2017/0042720 A1 | 2/2017 | Pavini | |
| 2017/0095392 A1 * | 4/2017 | Norton ....................... | B32B 5/18 |
| 2017/0348191 A1 * | 12/2017 | Salstein-Begley ..... | A61H 39/04 |
| 2018/0000495 A1 | 1/2018 | Pancholy | |
| 2018/0008284 A1 | 1/2018 | Saatchi et al. | |
| 2018/0070956 A1 | 3/2018 | Lampropoulos et al. | |
| 2018/0214160 A1 | 8/2018 | Hoskins et al. | |
| 2018/0280008 A1 * | 10/2018 | Okamura ............ | A61B 17/0057 |
| 2019/0029693 A1 | 1/2019 | Okamura | |
| 2019/0069904 A1 | 3/2019 | Harding et al. | |
| 2019/0090886 A1 | 3/2019 | Brown et al. | |
| 2020/0405320 A1 * | 12/2020 | Kawamoto ....... | A61B 17/12009 |
| 2021/0000481 A1 * | 1/2021 | Yamada .................. | A61F 5/013 |

FOREIGN PATENT DOCUMENTS

| | | |
|---|---|---|
| JP | 2010131296 A2 | 6/2010 |
| WO | 2017089843 A1 | 6/2017 |

OTHER PUBLICATIONS

U.S. Appl. No. 16/529,383, filed Aug. 1, 2019, naming inventor Castelli et al.

U.S. Appl. No. 62/818,530, filed Mar. 14, 2019, naming inventor Castelli.

Pancholy et al, "Prevention of Radial Artery Occlusion After Transradial Catheterization", JACC Cardiovascular Interventions, vol. 9, No. 19, Oct. 10, 2016, pp. 1992-1999.

Tian et al., "Ulnar Artery Compression: A Feasible and Effective Approach to Prevent the Radial Artery Occlusion after Coronary Intervention", Chinese Medical Journal, vol. 128, Issue 6, Mar. 20, 2015, pp. 795-798.

Hahalis et al., Radial Artery and Ulnar Artery Occlusions Following Coronary Procedures and the Impact of Anticoagulation: ARTEMIS (Radial and Ulnar ARTEry Occlusion Meta-AnalysIS) Systematic Review and Meta-Analysis, Journal of the American Heart Association, Aug. 23, 2017, 58 pp.

International Search Report and Written Opinion of International Application No. PCT/US2019/045069, dated Aug. 12, 2020, 20 pp.

* cited by examiner

DISTAL RADIAL COMPRESSION DEVICE

This application claims the benefit of U.S. Provisional Application Ser. No. 62/714,865, entitled "DISTAL RADIAL COMPRESSION DEVICE," and filed on Aug. 6, 2018, the entire content of which is incorporated herein by reference.

TECHNICAL FIELD

This disclosure relates to tissue compression devices.

BACKGROUND

Medical catheters may be advanced through an access site into vasculature of a patient to provide a lumen through which medical devices or therapeutic agents may be introduced to a treatment site. For example, the access site for percutaneous coronary procedures may include the radial artery or the femoral artery of a patient.

SUMMARY

Distal transradial percutaneous coronary procedures may include a vascular access site at a snuffbox of a hand of the patient. After a transradial percutaneous coronary procedure, pressure may be applied directly to tissue at the access site, e.g., at the snuffbox, to achieve patent hemostasis at the access site. The present disclosure describes a tissue compression device configured to apply pressure at the snuffbox. The compression device includes a base, a flexible backing adjustably mechanically connected to the base, and an expandable member mechanically connected to the flexible backing. The base includes a major surface configured to engage a palmar surface of a hand of a patient, for example, to position the hand of the patient in a predetermined configuration, and a plurality of base attachment structures extending from the major surface. The flexible backing is adjustably mechanically connected to the base via the plurality of base attachment structures, for example, to urge the hand of the patient into the predetermined configuration or to bring the expandable member into better engagement with the hand, by tightening the flexible backing to the base attachment structures of the base. The expandable member is configured to be positioned over the snuffbox of the hand of the patient and apply pressure to tissue at the snuffbox when the palmar surface of the hand is engaged with the major surface of the base.

In some examples, the disclosure describes a tissue compression device that includes a base, a plurality of base attachment structures, a flexible backing, and an expandable member. The base includes a major surface configured to engage a palmar surface of a hand of a patient. The plurality of base attachment structures extend from the major surface of the base. The flexible backing is adjustably mechanically connected to the plurality of base attachment structures. The expandable member is mechanically connected to the flexible backing. The expandable member is configured to be positioned over a snuffbox of the hand of the patient when the palmar surface of the hand is engaged with the major surface of the base and to apply pressure to tissue at the snuffbox.

In some examples, the disclosure describes a tissue compression device includes a base, a plurality of base attachment structures, a flexible backing, and an expandable member. The base is formed from a substantially rigid material and defines a major surface configured to engage a palmar surface of a hand of a patient to position the hand of the patient in a predetermined configuration. The plurality of base attachment structures extend from the major surface of the base. The flexible backing is formed from a substantially inextensible material and is adjustably mechanically connected to base via the plurality of base attachment structures. The expandable member is mechanically connected to the flexible backing. The expandable member is configured to be positioned over a snuffbox of a hand of a patient when the palmar surface of the hand is engaged with the major surface of the base and to inflate to apply pressure to selected tissue at the snuffbox.

In some examples, the disclosure describes a method that includes mechanically connecting a flexible backing of a tissue compression device to a first base attachment structure of a plurality of base attachment structures extending from a major surface of a base of the tissue compression device, where the first major surface is configured to engage a palmar surface of a hand of a patient. The method also includes mechanically connecting the flexible backing to a second base attachment structure of the plurality of base attachment structures. The flexible backing is configured to be adjustably mechanically connected to the base, and the tissue compression device further comprises an expandable member mechanically connected to the flexible backing. The expandable member is configured to be positioned over a snuffbox of the hand of the patient when the palmar surface of the hand is engaged with the major surface of the base and to apply pressure to selected tissue at the snuffbox.

The following clauses illustrate example subject matter described herein.

Clause 1: In some examples, a tissue compression device comprises a base comprising a major surface configured to engage a palmar surface of a hand of a patient; and a plurality of base attachment structures extending from the major surface; a flexible backing adjustably mechanically connected to the plurality of base attachment structures; and an expandable member mechanically connected to the flexible backing, wherein the expandable member is configured to be positioned over a snuffbox of the hand of the patient when the palmar surface of the hand is engaged with the major surface of the base, and wherein the expandable member is configured to apply pressure to tissue at the snuffbox.

Clause 2: In some examples of the tissue compression device of clause 1, the expandable member comprises a bladder configure to inflate to at least a pressure to cause patent hemostasis of a vascular access site at the snuffbox.

Clause 3: In some examples of the tissue compression device of clause 1 or clause 2, the expandable member comprises a transparent polymer.

Clause 4: In some examples of the tissue compression device of any one of clauses 1 through 3, the flexible backing comprises a plurality of backing attachment structures, wherein each respective backing attachment structure of the plurality of backing attachment structures is configured to adjustably secure the flexible backing to a respective base attachment structure of the plurality of base attachment structures.

Clause 5: In some examples of the tissue compression device of any one of clauses 1 through 4, at least one base attachment structure of the plurality of base attachment structures is continuous with the major surface.

Clause 6: In some examples of the tissue compression device of any one of clauses 1 through 5, at least one base attachment structure of the plurality of base attachment structures is physically separate from and attached to the major surface.

Clause 7: In some examples of the tissue compression device of any one of clauses 1 through 6, at least one base attachment structure of the plurality of base attachment structures extend away from the major surface in a direction parallel to or transverse to the major surface.

Clause 8: In some examples of the tissue compression device of any one of clauses 1 through 7, wherein the flexible backing comprises a substantially inextensible material.

Clause 9: In some examples of the tissue compression device of any one of clauses 1 through 8, at least one of the base or the flexible backing is configured to engage a left hand of the patient, a right hand of the patient, or both the left hand and right hand of the patient.

Clause 10: In some examples of the tissue compression device of any one of clauses 1 through 9, the base comprises a substantially rigid thermoplastic or a substantially rigid thermoset plastic.

Clause 11: In some examples of the tissue compression device of any one of clauses 1 through 10, the base comprises one or more support structures configured to reduce a range of motion of a digit of the hand or a portion of a wrist of the patient when the palmar surface of the hand is engaged with the major surface of the base.

Clause 12: In some examples of the tissue compression device of any one of clauses 1 through 11, the base is configured to position the hand of the patient in a predetermined configuration when the palmar surface of the hand is engaged with the major surface of the base.

Clause 13: In some examples of the tissue compression device of any one of clauses 1 through 12, the base comprises a pad configured to engage the palmar surface of the hand of the patient to position the hand of the patient in a predetermined configuration when the palmar surface of the hand is engaged with the major surface.

Clause 14: In some examples of the tissue compression device of clause 12 or 13, wherein the predetermined configuration is a grasped position.

Clause 15: In some examples of the tissue compression device of any one of clauses 1 through 14, wherein the expandable member is configured to be detached and subsequently reattached to the flexible backing.

Clause 16: In some examples, a tissue compression device comprises a base comprising a substantially rigid material, wherein the base comprises a major surface configured to engage a palmar surface of a hand of a patient to position the hand of the patient in a predetermined configuration; and a plurality of base attachment structures extending from the major surface; a flexible backing comprising a substantially inextensible material, the flexible backing being adjustably mechanically connected to base via the plurality of base attachment structures; and an expandable member mechanically connected to the flexible backing, wherein the expandable member is configured to be positioned over a snuffbox of a hand of a patient when the palmar surface of the hand is engaged with the major surface of the base, and wherein the expandable member is configured to inflate to apply pressure to selected tissue at the snuffbox.

Clause 17: In some examples of the tissue compression device of clause 16, the base is configured to position the hand of the patient in a predetermined configuration when the palmar surface of the hand is engaged with the major surface of the base.

Clause 18: In some examples of the tissue compression device of clause 16 or clause 17, the expandable member is configured to be detached and subsequently reattached to the flexible backing.

Clause 19: In some examples, a method includes mechanically connecting a flexible backing of a tissue compression device to a first base attachment structure of a plurality of base attachment structures extending from a major surface of a base of the tissue compression device, wherein the first major surface is configured to engage a palmar surface of a hand of a patient; and mechanically connecting the flexible backing to a second base attachment structure of the plurality of base attachment structures, wherein the flexible backing is configured to be adjustably mechanically connected to the base, and the tissue compression device further comprises an expandable member mechanically connected to the flexible backing, wherein the expandable member is configured to be positioned over a snuffbox of the hand of the patient when the palmar surface of the hand is engaged with the major surface of the base, and wherein the expandable member is configured to apply pressure to selected tissue at the snuffbox.

Clause 20: In some examples of the method of clause 19, the method further comprises positioning the palmar surface of the hand of the patient on the major surface of the base.

Clause 21: In some examples of the method of clause 20, positioning the palmar surface of the hand on the major surface of the base comprises positioning the palmar surface of the hand on the major surface of the base prior to mechanically connecting the flexible backing to the second base attachment structure.

Clause 22: In some examples of the method of clause 20, positioning the palmar surface of the hand on the major surface of the base comprises positioning the palmar surface of the hand on the major surface of the base after to mechanically connecting the flexible backing to the second base attachment structure.

Clause 23: In some examples of the method of any one of clauses 20 through 22, the method further comprises, after positioning the palmar surface of the hand of the patient on the major surface of the base, inflating the expandable member to cause patent hemostasis of a vascular access site at the snuffbox.

Clause 24: In some examples of the method of any one of clauses 20 through 23, the method further comprises, after positioning the palmar surface of the hand of the patient on the major surface of the base, adjusting a position of the expandable member relative to the hand of the patient.

Clause 25: In some examples of the method of clause 24, adjusting the position of the expandable member relative to the hand of the patient comprises loosening or tightening a connection between the flexible backing and at least one of the first or second base attachment structures.

Clause 26: In some examples of the method of clause 24, adjusting the position of the expandable member relative to the hand of the patient detaching the expandable member from the flexible backing and subsequently reattaching the expandable member to the flexible backing.

Clause 27: In some examples of the method of any one of clauses 19 through 26, the flexible backing comprises a plurality of backing attachment structures, and mechanically connecting the flexible backing to the first base attachment structure comprises adjustably mechanically connecting a first backing attachment structure of the plurality of backing attachment structures to the first base attachment structure of the plurality of base attachment structures, and wherein mechanically connecting the flexible backing to the second base attachment structure comprises adjustably mechanically connecting a second backing attachment structure of the plurality of backing attachment structures to the second base attachment structure of the plurality of base attachment structures.

Clause 28: In some examples of the method of any one of clauses 19 through 27, at least one base attachment structure of the plurality of base attachment structures is integrally formed with the major surface.

Clause 29: In some examples of the method of any one of clauses 19 through 28, at least one base attachment structure of the plurality of base attachment structures is physically separate from the major surface, and the method further comprises, before mechanically connecting the flexible backing to the first base attachment structure, attaching the at least one base attachment structure of the plurality of base attachment structures to the major surface.

Clause 30: In some examples of the method of any one of clauses 19 through 29, at least one base attachment structure of the plurality of base attachment structures extend away from the major surface in a direction parallel to or transverse to the major surface.

Clause 31: In some examples of the method of any one of clauses 19 through 30, the flexible backing comprises a substantially inextensible material.

Clause 32: In some examples of the method of any one of clauses 19 through 31, the base comprises one or more support structures configured to reduce the range of motion of a digit of the hand or a portion of a wrist of the patient when the palmar surface of the hand is engaged with the major surface of the base.

Clause 33: In some examples of the method of any one of clauses 19 through 32, the base is configured to position the hand of the patient in a predetermined configuration when the palmar surface of the hand is engaged with the major surface of the base.

Clause 34: In some examples of the method of any one of clauses 19 through 33, the method further comprises positioning a pad on the major surface of the base, the pad being configured position the hand of the patient in a predetermined configuration when the palmar surface of the hand is engaged with the major surface of the base.

Clause 35: In some examples of the method of any one of clauses 19 through 34, the method further comprises forming the base from a substantially rigid thermoplastic or a substantially rigid thermoset plastic.

Clause 36: In some examples of the method of any one of clauses 19 through 35, the method further comprises cutting the flexible backing from a substantially inextensible material.

Clause 37: In some examples of the method of any one of clauses 19 through 36, the method further comprises attaching the expandable member to the flexible backing by at least one of adhering, welding, or mechanically fastening the expandable member to the flexible backing.

Clause 38: In some examples of the method of any one of clauses 19 through 37, the expandable member comprises a transparent polymer.

The details of one or more examples are set forth in the accompanying drawings and the description below. Other features, objects, and advantages will be apparent from the description and drawings, and from the claims.

DETAILED DESCRIPTION

Figure 1A:
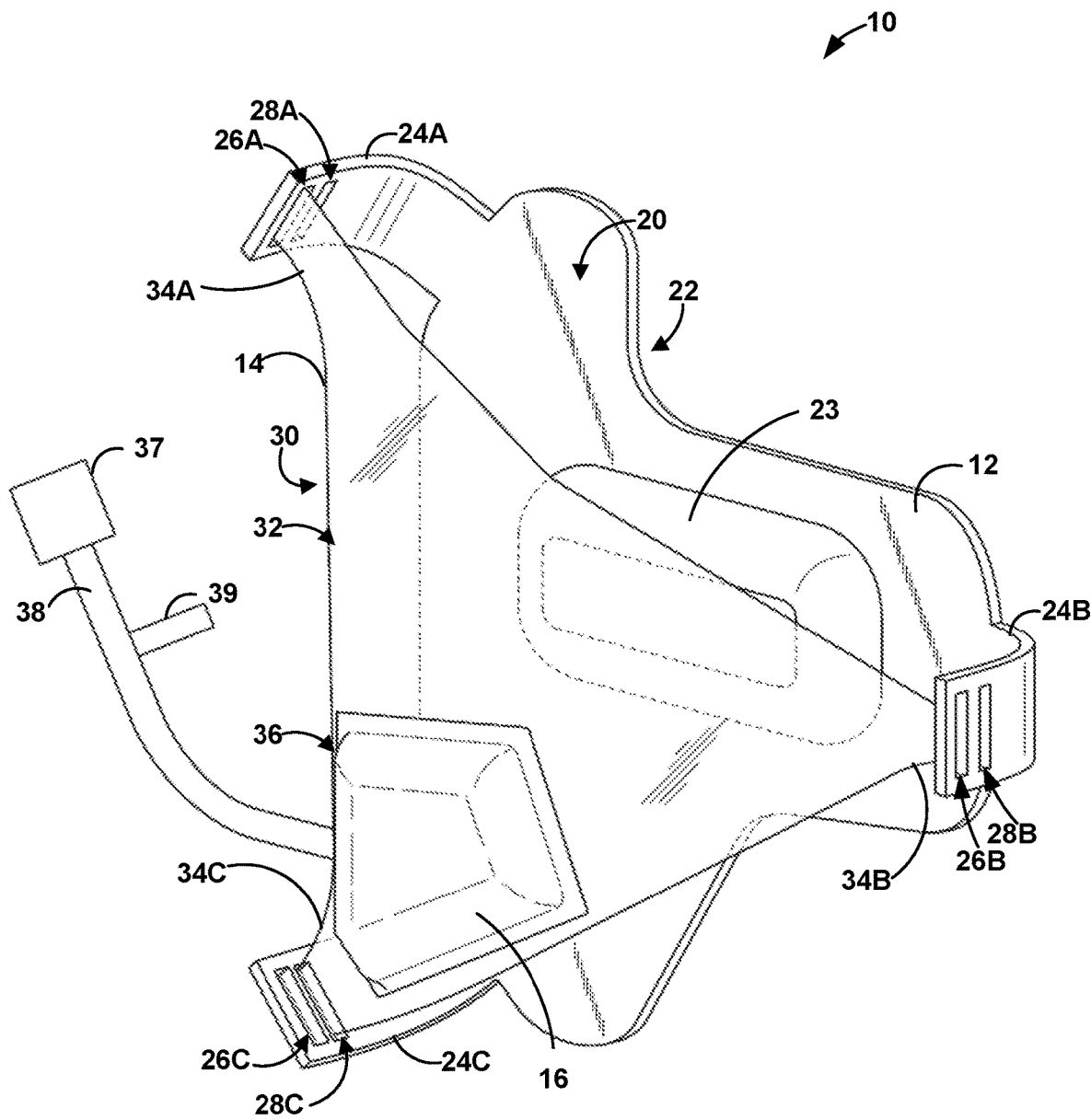
FIG. 1A is a conceptual perspective view of an example tissue compression device including a flexible backing adjustably mechanically connected to a base and an expandable member mechanically connected to the flexible backing.

The disclosure describes tissue compression devices and techniques to achieve patent hemostasis after a transradial percutaneous procedure with a vascular access site at a snuffbox of a hand of a patient. The snuffbox (also referred to as an anatomical snuffbox) is a triangular deepening on the radial, dorsal aspect of the hand at the level of the carpal bones, specifically, the scaphoid and trapezium bones forming the floor. Access to the vasculature via the snuffbox may include benefits compared to other access sites for transradial percutaneous procedures. For example, transradial access via the snuffbox may use a smaller incision compare to other access sites, such as, for example, transradial access proximal to the radial styloid process. The relatively smaller incision may reduce the pressure and/or time to achieve patent hemostasis, and thereby reduce post procedure recovery time.

Additionally, transradial access via the snuffbox provides an alternative access site in addition to other transradial access sites, such as, for example, proximal to the radial styloid process. By providing an additional access site, transradial access via the snuffbox may enable a patient to undergo a greater number of transradial percutaneous procedures by, for example, reducing non-occlusive radial artery injury. Also, by providing an additional access site, transradial access via the snuffbox may enable patients with anatomical limitations of the wrist to undergo transradial percutaneous procedures because transradial access via the snuffbox may present fewer nerves or other anatomical structures to be avoided compared to other access sites, such as, for example, proximal to the radial styloid process. Additionally, in some examples, access to a coronary artery of a patient via the snuffbox of the left hand radial artery of a patient may provide the advantage of less tortuous vasculature compared to the right hand radial artery of the patient.

After a transradial percutaneous coronary procedure, pressure may be applied to tissue at the access site, e.g., at or near the snuffbox, to achieve patent hemostasis at the access site. Example tissue compression devices described herein that are configured to apply pressure to tissue to help achieve patent hemostasis at the access site may include a base, a flexible backing adjustably mechanically connected to the base, and an expandable member mechanically connected to the flexible backing. The base and flexible backing may be configured to position the expandable member over a snuffbox and engage the hand of the patient. By engaging the hand of the patient, the tissue compression device may reduce movement of the expandable member relative to the snuffbox. In this way, the tissue compression device may be configured to apply pressure to selected tissue at the snuffbox beneath the expandable member. In some examples, pressure may be applied directly to the access site at the snuffbox. In other examples, pressure may be applied to the radial artery near the access site. The applied pressure may be sufficient to achieve patent hemostasis at the access site during or after a transradial percutaneous procedure.

In some examples, access to the radial artery at the snuffbox may require less pressure to achieve patent hemostasis compared to other access sites. For example, a pressure of approximately 2 pounds per square inch (psi) (13.8 kilopascal (kPa)) to approximately 8 psi (55.2 kPa) may be sufficient to achieve patent hemostasis of a vascular access site at the snuffbox, compared to a pressure greater than 8 psi (55.2 kPa) necessary to achieve patent hemostasis of a vascular access site located proximal to the snuffbox. In some examples, pressure may be indicated by a volume of air injected into a tissue compression device having an inflatable portion of a fixed volume. For example, approximately 2 cubic centiliters (cc) of air to approximately 5 cc of air may be sufficient to achieve patent hemostasis of a vascular access site at the snuffbox, compared to about 13 cc of air to about 18 cc of air necessary to achieve patent hemostasis of a vascular access site located proximal to the snuffbox. Additionally, or alternatively, using a vascular access site at the snuffbox may reduce the time to achieve patent hemostasis compared to other access sites and/or enable compression of the radial artery against soft tissue at the snuffbox compared to compression of the radial artery against rigid tissue, such as bone, at other access sites.

FIG. 1A is a conceptual perspective view illustrating an example tissue compression device 10 including a base 12, a flexible backing 14 adjustably mechanically connected to base 12, and an expandable member 16 mechanically connected to flexible backing 14. Tissue compression device 10 may be configured to receive and engage a hand of a patient to apply pressure to selected tissue at the snuffbox of the hand of the patient.

Figure 1B:
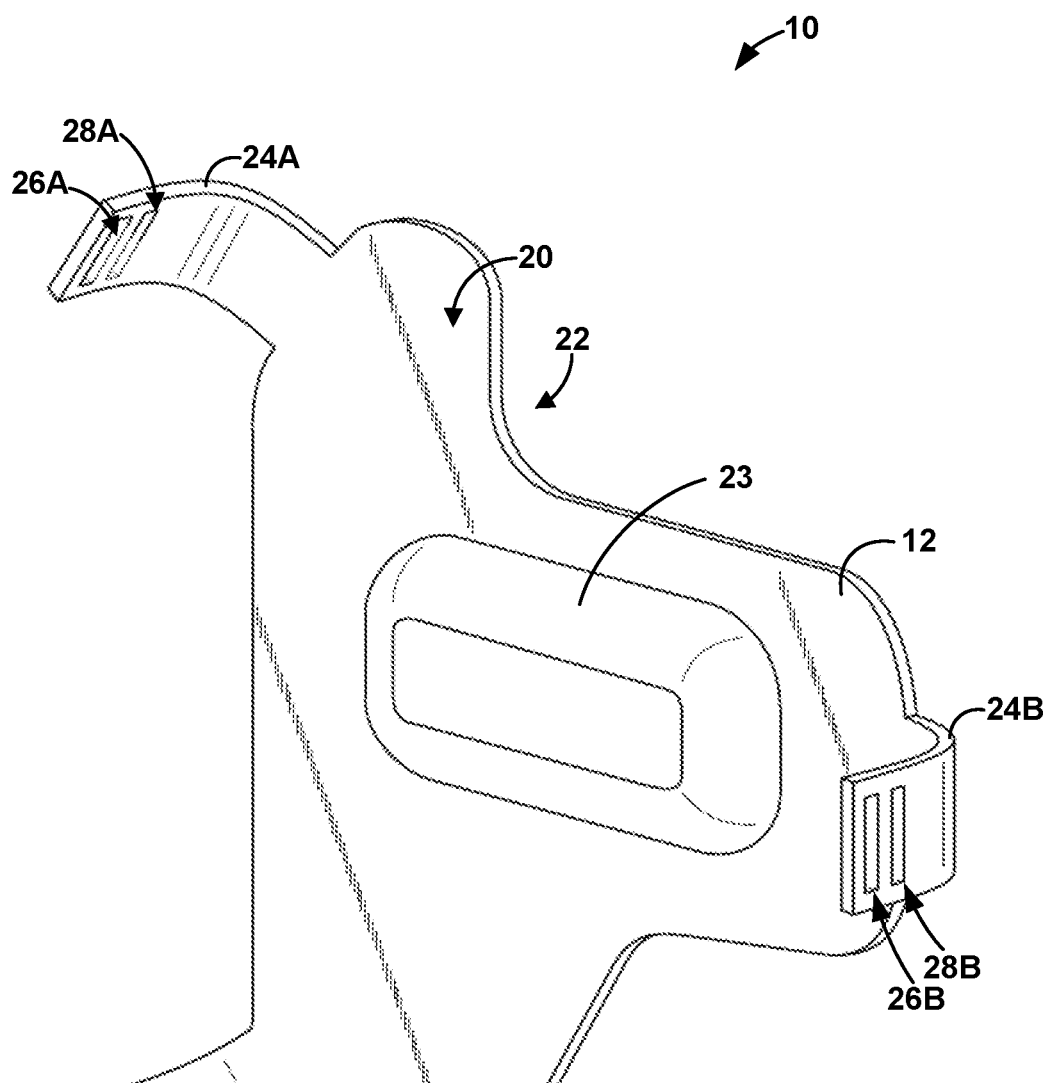
FIG. 1B is a conceptual perspective view of the base of the example tissue compression device illustrated in FIG. 1A.

FIG. 1B is a conceptual perspective view of the base of the example tissue compression device illustrated in FIG. 1A. FIG. 1B illustrates tissue compression device 10 without flexible backing 14 to provide an unobstructed view of base 12. Base 12 defines a first major surface 20 and a second major surface 22 on an opposite side of base 12 from first major surface 20. First major surface 20 and second major surface 22 face in different directions. First major surface 20 may include any suitable shape configured to engage with at least a portion of the hand of the patient. For example, as illustrated in FIGS. 1A and 1B, first major surface 20 may have a shape in the X-Y plane (orthogonal X-Y-Z axes are shown in the figures for ease of description only) that corresponds to an anatomical shape of a right hand or a left hand of a patient (e.g., mimics the general outline of the footprint of a hand or part of the footprint of the hand).

In some examples, first major surface 20 may have a shape in the X-Y plane that corresponds to an anatomical shape of both the right hand and the left hand of the patient, e.g., first major surface 20 may be ambidextrous. In other examples, first major surface 20 may have other shapes, such as circular, rectangular, or irregular shapes. In some examples, second major surface 22 may be shaped the same as or substantially similar to first major surface 20, which may permit second major surface 22 to be used to engage the other hand of a patient. For example, second major surface 22 may be a mirror image of the shape of first major surface 20 such that second major surface 22 has a shape that corresponds to an anatomical shape of either the right hand or the left hand of the patient and first major surface 20 has a shape that corresponds to an anatomical shape of the other of the left hand or the right hand of the patient. In this way, base 12 may be shaped to engage both the left hand of the patient and the right hand of the patient by flipping base 12 to engage the palmar surface of the hand of the patient with one of the first major surface 20 or second major surface 22.

Base 12 has a three-dimensional shape configured to position the hand of the patient in a predetermined configuration when a surface of the hand is positioned over first major surface 20 of base 12. The predetermined configuration may include, for example, a flat (e.g., the hand may sit flat on a planar surface) or a non-flat hand configuration, a partially bent position of one or more digits (e.g., fingers or the thumb) or the wrist of the patient (e.g., a cupped or grasped position), an extended position of one or more digits or the wrist of the patient, or a combination thereof. For example, the three-dimensional shape of base 12 may be such that first major surface 20 is shaped to correspond to a shape of a palmar surface of the hand of the patient in the predetermined configuration, such that base 12 includes one or more structures configured to correspond to the position of one or more digits or the wrist of the patient in the predetermined configuration, or both. By positioning the hand of the patient in a predetermined configuration, base 12 may improve comfort of the patient by allowing the hand of the patient to be positioned in a natural configuration while the patient is in a supine position, present the snuffbox area more prominently to reduce the time and/or pressure required to achieve patent hemostasis, or both, compared to other compression devices, such as bracelet or band type compression devices, which do not position the hand of the patient in a predetermined configuration.

In some examples, base 12 is formed from one or more substantially rigid materials. A substantially rigid material may include a material having an apparent modulus of rigidity (e.g., apparent shear modulus of elasticity) in ambient conditions sufficient to reduce deflection of base 12 by the hand of the patient before, during, or after a percutaneous coronary procedure. For example, a substantially rigid material may include a material having an apparent shear modulus of approximately 0.1 GPa. In some examples, base 12 includes one or more substantially rigid thermoplastics, such as acrylonitrile butadiene styrene (ABS), polyethylene, polycarbonate, polyamide, high impact polystyrene, polypropylene, or polyoxymethylene; or substantially rigid thermoset plastics, such as polyester, polyurethane, or epoxy resin. Additionally, base 12 may include one or more flexible regions or joints configured to improve patient comfort when tissue compression device 10 is retained on the hand of the patient.

In the example shown in FIGS. 1A and 1B, first major surface 20 is configured to face a palmar surface of the hand of the patient when tissue compression device 10 is retained on the hand of the patient. In some examples, first major surface 20 may be configured to engage with a palmar surface of the hand of the patient. For example, base 12 may be configured to support the hand of the patient, position the hand of the patient in a predetermined configuration, or both, when the hand is positioned over first major surface 20.

Second major surface 22 faces away from the hand of the patient when the palmar surface of the hand is facing first major surface 20. In some examples, second major surface 22 is configured to engage with one or more structures to limit mobility the hand of the patient when tissue compression device 10 is retained on the hand of the patient. For example, second major surface 22 may include bands, clips, straps, or the like configured to engage with a portion of an operating table or other device in a surgical suite to limit mobility the hand of the patient when retained in tissue compression device 10. By engaging with one or more structures to limit mobility the hand of the patient, tissue compression device 10 may enable a clinician to position the hand of the patient to present the snuffbox more prominently and improve accuracy of the arteriotomy.

In examples in which base 12 is ambidextrous, first major surface 20 or both first major surface 20 and second major surface 22 may be configured to both face the palmar surface of the hand of the patient or face away from the hand of the patient such that base 12 may be flipped to fit either the left or right hand.

In the example shown in FIGS. 1A and 1B, base 12 includes a pad 23 disposed on first major surface 20. Pad 23 may be configured to engage with a palmar surface of the hand of the patient when the hand is positioned over first major surface 20 to improve patient comfort. Additionally, or alternatively, pad 23 may be configured to position the hand of the patient in a predetermined configuration, as discussed above. For example, pad 23 may be positioned on base 12 and/or shaped to position the hand of the patient in the predetermined configuration. Pad 23 may include any suitable material, such as silicone, rubber, polyethylene, a viscoelastic material, or a thermoplastic or thermoset plastic, as discussed above. In some examples, pad 23 is formed from a softer, more pliable material than base 12.

In some examples, pad 23 may include an inflatable balloon configured to adjustably control the size and/or rigidity of pad 23. Adjustable control of the size and/or rigidity of pad 23 may enable tissue compression device 10 to accommodate different hand sizes or shapes and adjust the extent to which pad 23 extends from first major surface 20 to position the hand in a predetermined configuration, e.g., to present the snuffbox more prominently. Pad 23 may be integrally formed with base 12 or mechanically connected to base 12 by, for example, an adhesive, welding, a hook-and-loop fastener, or any other suitable mechanical fastener or combination of mechanical fasteners.

In other examples, base 12 may not include pad 23. For example, base 12 may be shaped, e.g., in the X-Z plane and/or Y-Z plane to include one or more curves, undulations, or other surface features to position the hand in a predetermined configuration, e.g., to present the snuffbox more prominently, to better grip the hand of the patient (by increasing static friction between the hand and base 12), or both. In addition, in some examples, base 12 includes a coating or other material applied to first major surface 20 (and second major surface 22 in some examples) to increase the static friction between the hand of the patient and base 12, which may reduce any undesirable relative movement between the patient's hand and base 12.

Flexible backing 14 is also helps reduce any undesirable relative movement between the patient's hand and base 12. Base 12 includes a plurality of base attachment structures 24A, 24B, and 24C (collectively, "base attachment structures 24") extending from first major surface 20. Base attachment structures 24 are configured to mechanically connect flexible backing 14 to base 12. As illustrated in FIGS. 1A and 1B, base attachment structures 24 may be configured to mechanically connect flexible backing 14 to first major surface 20 of base 12. In other examples, base attachment structures 24 may be configured to enable flexible backing 14 to be attached to both first major surface 20 and second major surface 22, such as in examples in which base 12 may be shaped to engage both the left hand of the patient and the right hand of the patient by flipping (e.g., inverting) base 12 to engage the palmar surface of the hand of the patient with one of the first major surface 20 or second major surface 22.

Mechanically connecting flexible backing 14 to base 12 may enable tissue compression device 10 may better engage the hand of the patient. For example, base attachment structures 24 may enable flexible backing 14 to be tightened on to the hand of the patient prior to or after inflating expandable member 16. Tightening flexible backing 14 to the hand of the patient prior to or after inflating expandable member 16 may maintain a position of expandable member 16 over the snuffbox while expandable member 16 is inflated. Maintaining the position of expandable member 16 over the snuffbox may more accurately direct pressure to tissue at the snuffbox to reduce the amount of pressure and/or time to achieve patent hemostasis. Additionally, tightening flexible backing 14 to the hand of the patient prior to or after inflating expandable member 16 may provide pre-compression of tissue at the snuffbox to reduce the amount of pressure exerted by expandable member 16 to achieve patent hemostasis.

Although three base attachment structures 24 are shown in FIGS. 1A and 1B, in other examples, base 12 may include a fewer or greater number of base attachment structures (e.g., only two base attachment structures or more than three base attachment structures). In some examples, base attachment structures 24 may be continuous with (e.g., integrally formed with) the part of base 12 defining first major surface 20 or physically separate from and mechanically connected to the part of base 12 defining first major surface 20 by, for example, welding, an adhesive, or any other suitable fastener. In an "at rest" state in which no external forces (other than naturally occurring forces) are applied to base attachment structures 24, base attachment structures 24 may extend away from first major surface 20 in any suitable direction, such as parallel to or transverse to first major surface 20. In the example of FIGS. 1A and 1B, base attachment structures 24 define protrusions that are continuous with first major surface 20 and extend away from first major surface 20 in a direction substantially transverse to first major surface 20.

Flexible backing 14 may be directly or indirectly mechanically connected to attachment structures 24 using any suitable technique. In some examples, a hand of a patient may be placed on base 12 and flexible backing 14 may be subsequently connected to base attachment structures 24. In other examples, the hand of the patient may be inserted or removed from the region defined by the base 12 and flexible backing 14 while flexible backing 14 is connected to base attachment structures 24. For example, when connected, base 12 and flexible backing 14 may define an opening therebetween through which the hand of the patient may be introduced between base 12 and flexible backing 14.

In some examples, base attachment structures 24 may be configured to receive flexible backing 14. For example, in the example shown in FIGS. 1A and 1B, base attachment structures 24 define respective first slots 26A, 26B, and 26C (collectively, "first slots 26"), and respective second slots 28C, 28B, and 28C (collectively, "second slots 28"). Each respective first and second slots of first and second slots 26 and 28 enable the respective attachment structure of base attachment structures 24 to adjustably mechanically connect flexible backing 14 to base 12. For example, each pair of slots 26A and 28A, 26B and 28B, 26C and 28C may define a ladder tension lock, a triglide slide, or other suitable fastening system configured to adjustably mechanically connect to at least a portion of flexible backing 14.

In some examples, in addition to or instead of base attachment structures 24, another part of base 12 may define one or more base attachment structures configured to receive flexible backing 14 and secure flexible backing relative to base 12. For example, first major surface 20 may define one or more holes or slots defining, for example, a ladder tension lock, a triglide slide, or the like. In other examples, base attachment structures 24 may include any suitable attachment device configured to secure at least a portion of flexible backing 14 to base 12, such as belts, buckle, buttons, clips, or the like.

Flexible backing 14 is configured to engage the hand of a patient when tissue compression device 10 is retained on the hand to urge the hand toward first major surface 20, e.g., to hold the hand of the patient in a predetermined configuration, and to bring expandable member 16 into engagement with tissue of the patient to help achieve patient hemostasis. In the example shown in FIG. 1A, flexible backing 14 defines a first major surface 30 and second major surface 32 and includes a plurality of backing attachment structures 34A, 34B, and 34C (collectively, "backing attachment structures 34").

Flexible backing 14 may include any suitable shape to engage with at least a portion of the hand of the patient. For example, as illustrated in FIG. 1A, major surfaces 30, 32 of flexible backing 14 are shaped to engage with the dorsal surface (opposite the palmar surface) of a hand of a patient, e.g., may have a shape that corresponds to the anatomical shape of a right hand of a patient. In other examples, flexible backing 14 may be shaped to engage with a left hand of the patient or both the left and the right hand of the patient, e.g., flexible backing 14 may be ambidextrous. In some examples, flexible backing 14 may at least partially conform to a shape of a dorsal surface, radial border, and/or ulnar border of the hand of the patient when a palmar surface of the hand faces first major surface 20 of base 12. By at least partially conforming to the hand of the patient, flexible backing 14 may allow tissue compression device 10 to engage the hand of the patient to position the hand in the predetermined configuration, as discussed above.

Flexible backing 14 includes one or more flexible biocompatible materials. For example, flexible backing 14 may include one or more polymers, such as acrylonitrile butadiene styrene (ABS), polyethylene, polycarbonate, polyamide, high impact polystyrene, polypropylene, polyester, polyurethane, polyvinyl chloride, nitrile, or epoxy resin. In some examples, flexible backing 14 includes a transparent material, such as polypropylene. A fully or partially (e.g., a transparent window can be defined in backing 14) transparent flexible backing 14 may enable a clinician to visualize an access site while tissue compression device 10 is retained on the hand of the patient. In contrast, if expandable member 16 was fully opaque, the clinician would not be able to view the access site. By visualizing the access site, the clinician may visually confirm patent hemostasis.

In some example, flexible backing 14 includes a substantially inextensible material. A substantially inextensible material may include a material that breaks after being extended between about 10% and about 100% (as measured in accordance with ASTM Standard D638), with a tensile strength between about 20 MPa and about 50 MPa (as measured in accordance with ASTM Standard D412), and/or with an elastic modulus between about 0.1 GPa and about 1 GPa (as measured in accordance with ASTM Standard E2769). For example, when tissue compression device 10 is retained on the hand of the patient, increasing pressure in expandable member 16 (e.g., inflating expandable member 16) results in increasing pressure on tissue at the snuffbox of the hand of the patient, rather than resulting in elongation or stretching of flexible backing 14. In this way, flexible backing 14 may conform to a dorsal surface of the hand of the patient, and reduce elongation or stretching of flexible backing 14 when expandable member 16 is inflated.

First major surface 30 of backing 14 is configured to face a dorsal surface of the hand of the patient when tissue compression device 10 is retained on the hand of the patient such that a palmar surface of the hand faces base 12. That is, the hand of the patient may be positioned between first major surface 30 of backing 14 and base 12. In some examples, first major surface 30 may be configured to engage with a dorsal surface of the hand of the patient. For example, flexible backing 14 may be configured to urge the hand of the patient toward base 12 to position the hand of the patient in the predetermined configuration when flexible backing 14 is tightened via base attachment structures 24 and backing attachment structures 34.

Second major surface 32 is configured to face away from the hand of the patient when tissue compression device 10 is retained on the hand of the patient such that a palmar surface of the hand faces base 12. In examples in which flexible backing 14 is ambidextrous, first major surface 30 and second major surface 32 may be configured to both face the dorsal surface of the hand of the patient and face away from the hand of the patient, such that flexible backing 14 may be flipped to fit either the left or right hand.

As illustrated in FIG. 1A, flexible backing 14 includes backing attachment structures 34. Each respective backing attachment structure of backing attachment structures 34 may be configured to adjustably secure flexible backing 14 to a respective attachment structure of base attachment structures 24. For example, backing attachment structure 34A includes a strap configured to adjustably mechanically connect flexible backing 14 to base attachment structure 24A that includes a tension ladder. Similarly, respective backing attachment structures 34B and 34C include respective straps configured to adjustably mechanically connect flexible backing 14 to respective base attachment structures 24B and 24C. In other examples, respective backing attachment structures 34 may include any suitable corresponding structure configured to mechanically connect to respective base attachment structures 24. In some examples, one or more backing attachment structures of backing attachment structures 34 may enable flexible backing 14 to be tightened on to the hand of the patient prior to or after inflating expandable member 16. In this way, flexible backing 14 may allow tissue compression device 10 to engage the hand of the patient to position the hand of the patient in the predetermined configuration.

In some examples, backing attachment structures 34 and base attachment structures 24 are positioned on flexible backing 14 and base 12, respectively, to provide substantially uniform distribution of force from flexible backing 14 to the hand of the patient when tissue compression device 10 is retained on the hand of the patient. For example, when tissue compression device 10 is retained on the hand of the patient such that the palmar surface faces base 12 and after tightening flexible backing 14 using backing attachment structures 34 and base attachment structures 24, flexible backing 14 may provide a substantially uniform compressive force to at least a portion of the dorsal surface of the hand of the patient. Uniform distribution of force from flexible backing 14 to the hand of the patient may improve patient comfort, enable expandable member 16 to provide a substantially uniform compressive force to selected tissue at the snuffbox of the hand of the patient, or both.

Expandable member 16 is configured to be positioned over the snuffbox of the hand of the patient when tissue compression device 10 is retained on the hand such that the palmar surface of the hand faces base 12. For example, expandable member 16 may be secured in place to flexible backing 14 at a location that positions expandable member 16 over the snuffbox when tissue compression device 10 is retained on the hand of the patient such that the palmar surface of the hand faces base 12. In some examples, expandable member 16 may be removably secured to flexible backing 14 such that a clinician may adjust the position of expandable member 16 relative to flexible backing 14 prior to retaining tissue compression device 10 on that hand of the patient. For example, expandable member 16 may be connected to backing 14 via an adhesive, such as a pressure-sensitive adhesive or a removable adhesive, or a mechanical fastener, such as a loop and hook mechanism, and a clinician may detach expandable member 16 from backing 14 by pulling expandable member 16 away from backing 14 and then subsequently use the adhesive or loop and hook mechanism to reattach expandable member 16 to backing 14 at a different location.

In addition to or instead of the adhesive or a loop and hook mechanism, in some examples, backing attachment structures 34 may be configured to adjust the position of expandable member 16 relative to the hand of the patient when tissue compression device 10 is retained on the hand of the patient to position expandable member 16 over the snuffbox. For example, a clinician may adjust one or more backing attachment structures 34 to move the position of expandable member 16 relative to the hand of the patient and position expandable member 16 over the snuffbox.

Expandable member 16 may be mechanically connected to flexible backing 14 by any suitable means, such as, for example, an adhesive, thermal bonding, welding, or a mechanical fastener, e.g., by a hook-and-loop fastener. In other examples, expandable member 16 may be integrally formed with flexible backing 14. For example, flexible backing 14 may include two or more layers forming a pocket and defining expandable member 16.

In some examples, expandable member 16 includes a transparent material, such as polypropylene. A transparent expandable member 16 may enable a clinician to visualize an access site while tissue compression device 10 is retained on the hand of the patient. In contrast, if expandable member 16 was opaque, the clinician would not be able to view the access site. By visualizing the access site, the clinician may visually confirm patent hemostasis.

Expandable member 16 is configured to apply pressure to tissue at the snuffbox when tissue compression device 10 is retained on the hand of the patient (such that the palmar surface faces base 12) to help achieve patent hemostasis at the access site. Expandable member 16 define any suitable shape having any suitable surface area to apply pressure to selected tissue at the snuffbox. For example, as illustrated in FIG. 1A, a major surface of expandable member 16 configured to engage with a snuffbox of a hand of a patient while the palmar surface of the hand rests on base 12 defines a pentagon. In other examples, this surface of expandable member 16 may define other geometric or irregular shapes. Additionally, expandable member 16 define any suitable volume to achieve a selected pressure on the selected tissue at the snuffbox. For example, expandable member, when in a deflated configuration or an inflated configuration, may extend any suitable distance from first major surface 30 of flexible backing 14.

As illustrated in FIG. 1A, expandable member 16 includes a bladder 36 fluidly connected to a channel 38. Channel 38 may be fluidly connected to one or more inflation devices 37 configured to inflate bladder 36 and one or more deflation devices 39 configured to deflate bladder 36. For example, inflation device 37 may include a pump configured to controllably inflate bladder 36 of expandable member 16 or a syringe configured to controllably inflate bladder 36.

Deflation device 39 may include a release valve configured to deflate bladder 36. In some examples, after achieving patent hemostasis, a clinician may use deflation device 39 to uncontrollably and fully deflate bladder 36, e.g., prior to removing tissue compression device 10 from the hand of the patient. In other examples, deflation device 39 may more controllably deflate bladder 36. For example, a clinician may inflate bladder 36 using inflation device 37 to a first pressure that is greater than a minimum pressure to achieve patent hemostasis, e.g., the clinician may inflate bladder 36 until the clinician visually confirms stoppage of blood flow from the access site. After inflating bladder 36 to the first pressure, the clinician may controllably deflate bladder 36 using deflation device 39 to a second pressure slightly less than the minimum pressure to achieve patent hemostasis, e.g., the clinician may deflate bladder 36 until the clinician visually confirms return blood flow from the access site. After deflating bladder 36 to the second pressure, the clinician may inflate bladder 36 by a predetermined volume, such as, for example, 1 cubic centimeter to 2 cubic centimeters of air, to a third pressure and confirm stoppage of blood flow. In some examples, the third pressure may be sufficient to achieve patent hemostasis, while preventing occlusion of the vasculature, e.g., occlusion of the radial artery. By controllably deflating bladder 36 to the second pressure, the clinician may more accurately inflate bladder 36 to the third pressure to reduce occlusion of the radial artery while still achieving patent hemostasis of the access site.

Bladder 36 may define a first major surface facing base 12 and is configured to inflate to at least a pressure that provides patent hemostasis of vasculature at the snuffbox. In some examples, inflation of bladder 36 will tend to move the first major surface of bladder 36 away from first major surface 30 of flexible backing 14 and toward first major surface 20 of base 12. When tissue compression device 10 is retained on a hand of the patient, inflation of bladder 36 forces the first major surface of bladder 36 against the tissue at the snuffbox to provide compression of selected tissue in contact with the first major surface of bladder 36. In this way, expandable member 16 may inflate to apply a selected pressure to tissue at the snuffbox.

Figure 2:
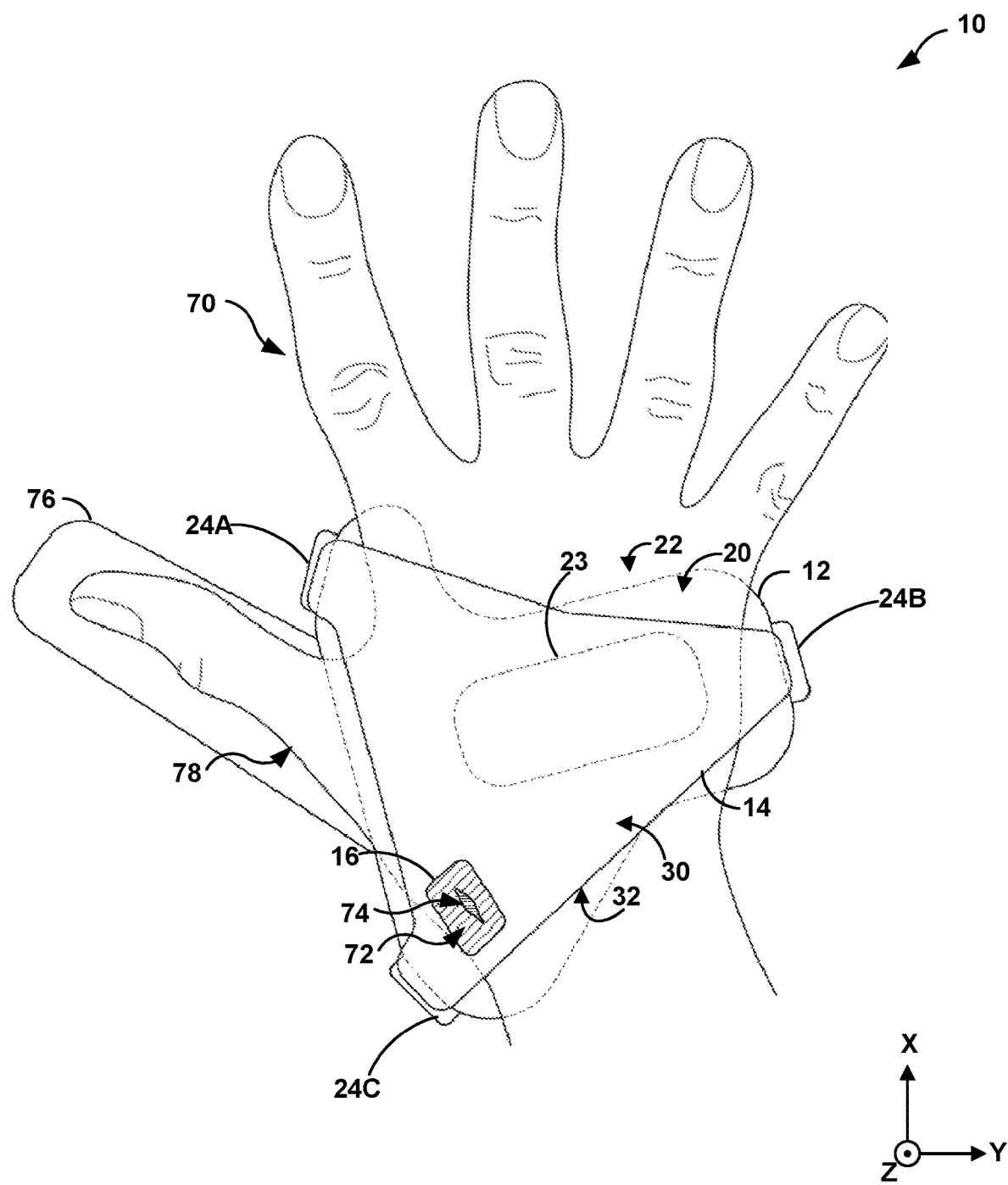
FIG. 2 is a conceptual plan view illustrating the example tissue compression device of FIG. 1A retained on a hand of a patient.

FIG. 2 is a conceptual plan view illustrating an example tissue compression device 10 retained on hand 70 of a patient. As illustrate in FIG. 2, tissue compression device 10 is configured to engage hand 70 to compress a vascular access site 74 (e.g., providing access into a radial artery of the patient) at snuffbox 72 of hand 70. Base 12 is shaped to engage the anatomical shape of hand 70. In addition, in the example shown in FIG. 2, first major surface 20 of base 12 is shaped to support at least a portion of the wrist of the patient and at least a portion of the palmar surface of hand 70.

As discussed above, in some examples, base 12 may include one or more support structures configured to reduce the range of motion of a digit or a portion of a wrist of the hand of the patient when the palmar surface of the hand is engaged with first major surface 20 of base 12. For example, as illustrated in FIG. 2, base 12 includes support structure 76. Support structure 76 is configured to support thumb 78 of the patient. By supporting thumb 78, tissue compression device 10 may engage hand 70 to retain thumb 78 in a dorsal-radial direction to present snuffbox 72 more prominently. In other examples, base 12 may support hand 70, for example, to position other portions of hand 70, such as the fingers or wrist of the patient, in a predetermined configuration.

Figure 3:
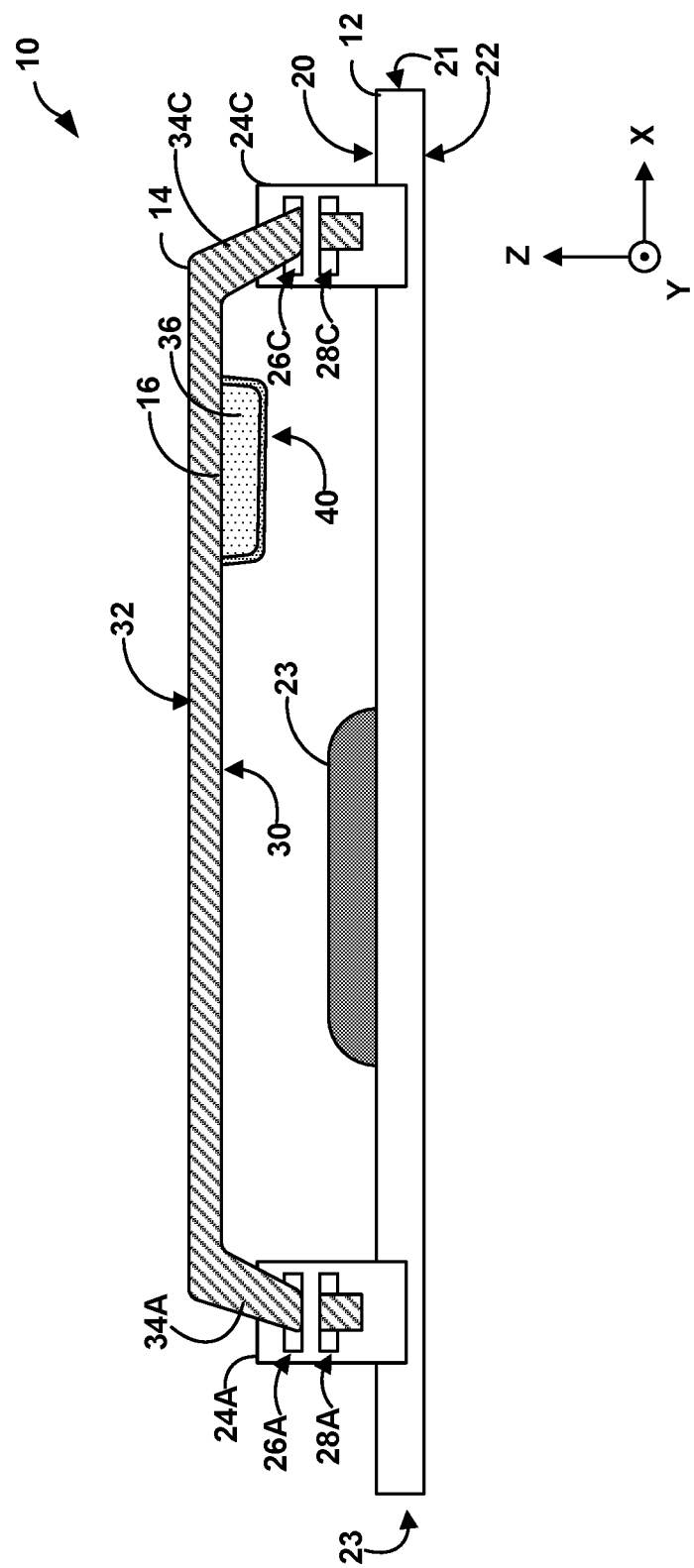
FIG. 3 is a conceptual side view illustrating the example tissue compression device of FIG. 1A.

FIG. 3 is a conceptual side view illustrating the example tissue compression device 10 of FIGS. 1A and 1B. As illustrated in FIG. 3, base 12 is substantially flat such that first major surface 20, extending from a first end 21 to a second end 25, is substantially planar (e.g., planar or nearly planar to the extent permitted by manufacturing and material tolerances). Expandable member 16 is mechanically connected to a side of flexible backing 14 configured to face base 12 and is configured to be positioned over a snuffbox of a hand of the patient and to apply pressure to tissue at the snuffbox when the palmar surface of the hand faces and is positioned over first major surface 20 of base 12.

In some examples, bladder 36 of expandable member 16 defines a first major surface 40 facing base 12. Inflation of bladder 36 will tend to move first major surface 40 of bladder 36 away from first major surface 30 of flexible backing 14 and toward first major surface 20 of base 12. When tissue compression device 10 is retained on a hand of the patient such that the palmar surface faces first major surface 20 of base 12, inflation of bladder 36 forces first major surface 40 of bladder 36 against the tissue at the snuffbox to provide compression of selected tissue in contact with first major surface 40 of bladder 36. In this way, tissue compression device may compress selected tissue at the snuffbox of the hand of the patient to achieve patent hemostasis of a vasculature access site at the snuffbox. As discussed above, major surface 40 of expandable member 16 may define any suitable shape (e.g., a pentagon, a circle, an octagon, and the like) configured to engage with the target tissue region (e.g., a snuffbox) of patient.

Figure 1B:
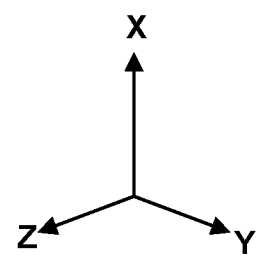
Figure 4:
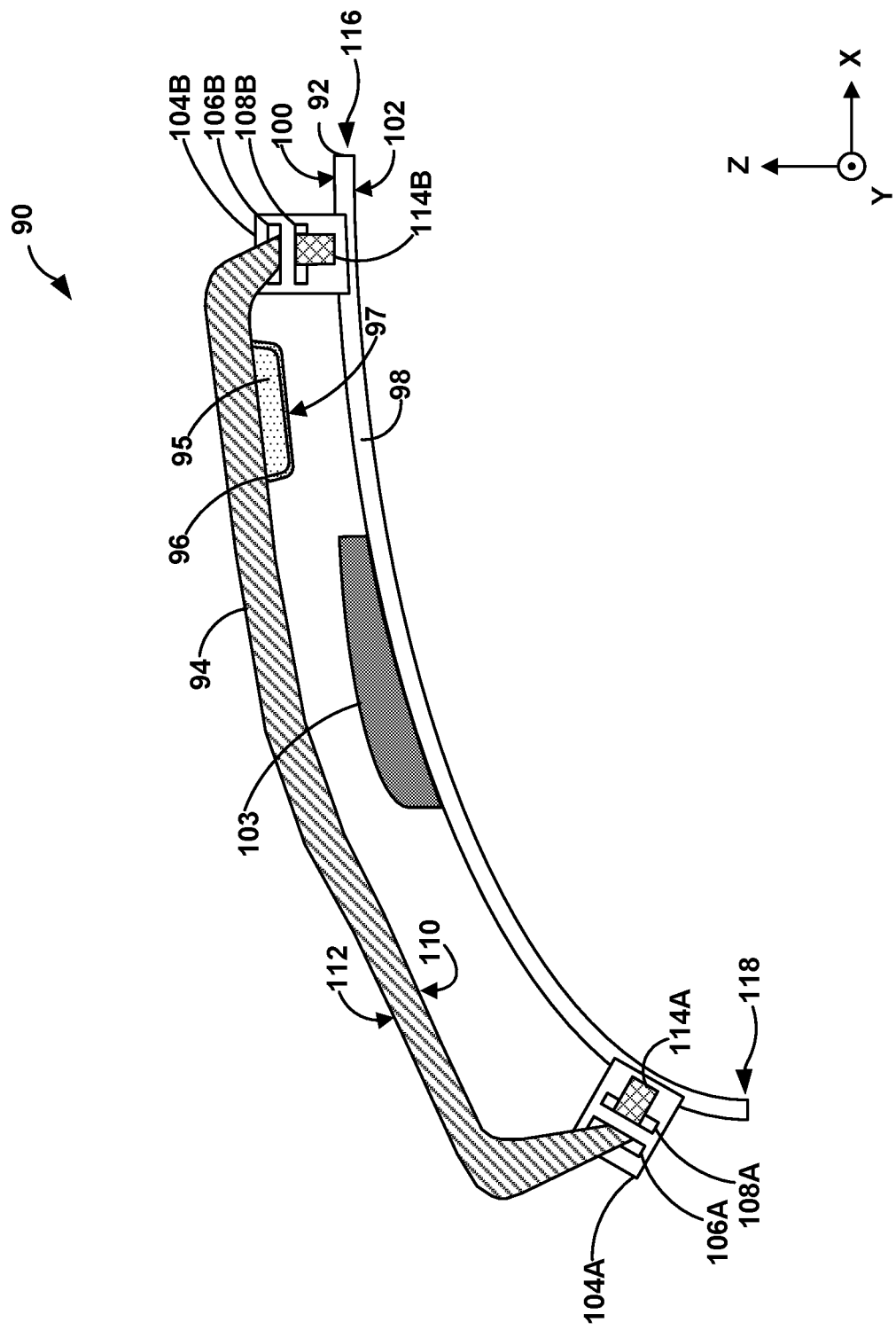
FIG. 4 is a conceptual side view illustrating an example tissue compression device including a curved base.

In some examples, base 12 of tissue compression device 10 may be curved to better position hand 70 in a predetermined configuration. For example, FIG. 4 is a conceptual side view illustrating an example tissue compression device 90 including a curved base 92. Tissue compression device 90 may be the same as, or substantially similar to, tissue compression device 10 illustrated in FIGS. 1 and 2. For example, tissue compression device 90 includes a base 92, a flexible backing 94 adjustably mechanically connected to base 92, and an expandable member 96 mechanically connected to flexible backing 94, which may be similar to the like-named elements in FIGS. 1A and 1B.

Base 92 defines a first major surface 100 and a second major surface 102 opposite first major surface 100, a pad 103, and a plurality of base attachment structures 104A and 104B (collectively, "base attachment structures 104"). Base attachment structures 104 include first slots 106A and 106B, and second slots 108A and 108B. Each pair of slots 106A and 108A, and 106B and 108B, may define a ladder tension lock configured to adjustably secure flexible backing 94 to base 92. Flexible backing 94 defines a first major surface 110 and second major surface 112 opposite first major surface 110, and includes a plurality of backing attachment structures 114A and 114B (collectively, "backing attachment structures 114").

Expandable member 96 is mechanically connected to flexible backing 94 and configured to be positioned over a snuffbox of a hand of the patient and to apply pressure to tissue at the snuffbox when the palmar surface of the hand faces and is positioned over first major surface 100 of base 92. In some examples, expandable member 96 includes a bladder 95 defining a first major surface 97 facing base 92. Inflation of bladder 95 will tend to move first major surface 97 of bladder 95 away from first major surface 110 of flexible backing 94 and toward first major surface 100 of base 92. When tissue compression device 90 is retained on a hand of the patient such that the palmar surface faces first major surface 100 of base 92, inflation of bladder 95 forces first major surface 97 of bladder 95 against the tissue at the snuffbox to provide compression of selected tissue in contact with first major surface 97 of bladder 95.

As illustrated in FIG. 3, base 92 is curved, such that first major surface 100 is non-planar. First major surface 100 extends from a first end 116 to a second end 118. Base 92 defines a gradual 90-degree curve from first end 116 to second end 118. Base 92 may define any suitable curve having any suitable curvature (e.g., between about 0-degrees to about 180-degrees, such as between about 0-degrees to about 90 degrees) and any suitable rate of curvature along any portion of base 92 between first end 116 and second end 118. In this way, tissue compression device 90 may be shaped to correspond to an anatomical shape of the hand of the patient to comfortably engage with the hand when the hand is held in a predetermined configuration.

As illustrated in FIG. 4, in some examples, second major surface 102 is curved to substantially correspond to the curve of first major surface 100, e.g., such that a thickness of base 12 from first major surface 100 to second major surface 102 is substantially constant from first end 116 to second end 118. In other examples, second major surface 102 may be substantially planar, e.g., a planar or nearly planar surface extending from first end 116 to second end 118. A planar second major surface 102 may enable second major surface 102 to be placed on a flat resting surface, which may contribute to the stability of tissue compression device 90 on the resting surface. In other examples, one or more protrusions may extend from second major surface 102. The one or more protrusions may be continuous with second major surface 102 or separate from and attached to second major surface 102. The one or more protrusions may extend away from second major surface 102 in a direction transverse to second major surface 102 such that tissue compression device 90 may be placed on a flat resting surface (e.g., with the second major surface 102 facing the flat surface), which may contribute to the stability of tissue compression device 90 on the resting surface.

Figure 5:
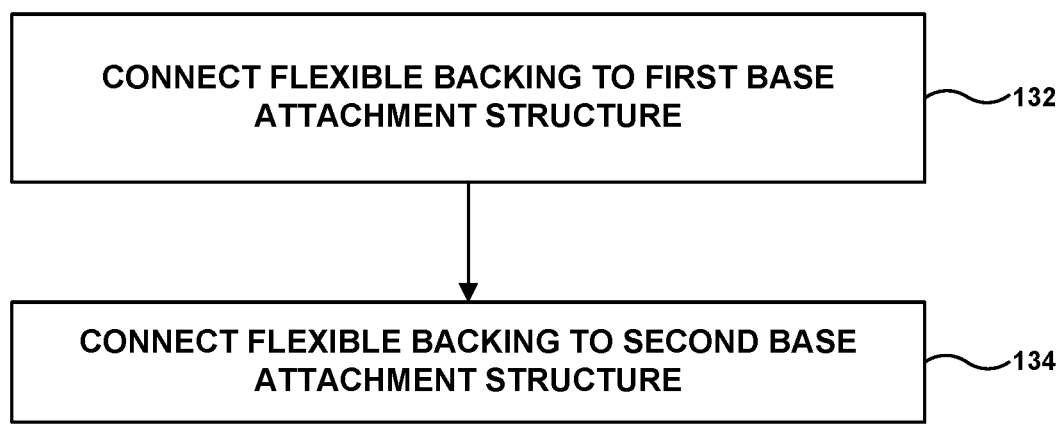
FIG. 5 is a flow diagram illustrating an example method of assembling a tissue compression device including a flexible backing adjustably mechanically connected to a base and an expandable member mechanically connected to the flexible backing.

The tissue compression devices described herein may be assembled using any suitable technique. FIG. 5 is a flow diagram illustrating an example method of assembling an example tissue compression device including a base, a flexible backing adjustably mechanically connected to the base, and an expandable member mechanically connected to the flexible backing. The tissue compression device may be the same as or substantially similar to tissue compression devices 10 and 90 discussed above with respect to FIGS. 1-3. Although FIG. 5 is described with respect to tissue compression device 10, in other examples, the method of FIG. 5 may be used to assemble tissue compression device 90 or another tissue compression device including a flexible backing adjustably mechanically connected to a base and an expandable member mechanically connected to the flexible backing.

In accordance with the method shown in FIG. 5, a user or device mechanically connects flexible backing 14 of tissue compression device 10 to first base attachment structure 24A of a plurality of base attachment structures 24 extending from first major surface 20 of base 12 of tissue compression device 10 (132), such as by feeding backing attachment structure 34A through openings slots 26A, 28A in first base attachment structure 24A. The method also includes mechanically connecting the flexible backing to a second base attachment structure 24B of the plurality of base attachment structures 24 (134), such as by feeding backing attachment structure 34B through openings slots 26B, 28B in second base attachment structure 24B. Flexible backing 14 may be mechanically connected to base 12 using the technique shown in FIG. 5 before or after the palmar surface of the hand of the patient is positioned on first major surface 20.

In some examples, after flexible backing 14 is connected to base 12 and while the palmar surface of the hand of the patient is engaged with first major surface 20 of base 12, the user may tighten flexible backing 14 onto the back surface of the patient's hand in order to bring expandable member 16 into better engagement with the tissue of the patient. For example, the user may pull backing attachment structures 34A, 34B further through the respective slots 26A, 28A and 26B, 28B.

In some examples, the method of FIG. 5 may be part of a method of forming or assembly device 10 and may further include, before mechanically connecting the flexible backing to the base, thermoforming or molding base 12. Base 12 may include a substantially rigid thermoplastic configured to be thermoformed to substantially conform to an anatomical shape of the hand of the patient or a substantially rigid thermoset plastic configured to be molded to substantially conform to an anatomical shape of the hand of the patient. By thermoforming or molding base 12 to conform to an anatomical shape of the hand of the patient, base 12 may be shaped to improve patient comfort and/or present the snuffbox more prominently.

In some examples, base 12 is configured to position the hand of the patient in a predetermined configuration when the palmar surface of the hand is engaged with first major surface 20 of base 12, e.g., a grasped position, using a selected shape of first major surface 20, pad 23, and/or support structures. In examples in which base 12 includes pad 23 disposed on base 12, assembling tissue compression device 10 may include positioning pad 23 on base 12 such that pad 23 is configured to engage the palmar surface of the hand of the patient to position the hand of the patient in the predetermined configuration when the palmar surface of the hand is engaged with first major surface 20 of base 12. In examples in which base 12 includes one or more support structures, assembling tissue compression device 10 may include attaching the one or more supporting structures to base 12 such that the one or more supporting structures are configured to reduce the range of motion of a digit of the hand or a portion of a wrist of the patient when the palmar surface of the hand is engaged with first major surface 20 of base 12 to help keep the hand in the predetermined configuration.

As discussed above, base 12 may include at least one base attachment structure 24 that is integrally formed with the first major surface 20. In other examples, assembling tissue compression device 10 may include attaching at least one base attachment structure of the plurality of base attachment structures 24 that is physically separate from first major surface 20 to first major surface 20. In some examples, at least one attachment structure of the plurality of base attachment structures extend away from the major surface in a direction parallel to and/or transverse to the major surface.

Figure 6:
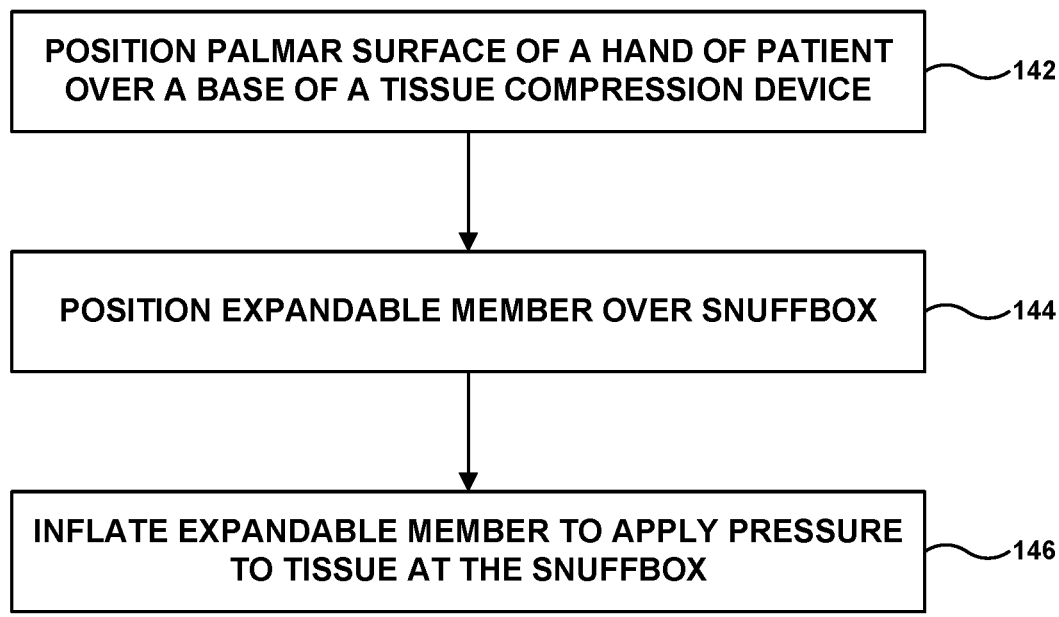
FIG. 6 is a flow diagram illustrating an example method of using a tissue compression device including a flexible backing adjustably mechanically connected to a base and an expandable member mechanically connected to the flexible backing to a patient.

The tissue compression devices describe herein may be retained on a hand of a patient using any suitable technique. FIG. 6 is a flow diagram illustrating an example method of using a tissue compression device including a base, a flexible backing adjustably mechanically connected to the base, and an expandable member mechanically connected to the flexible backing to a patient. The tissue compression device may be the same as or substantially similar to tissue compression devices 10 and 90 discussed above with respect to FIGS. 1-4. Although FIG. 6 is described with respect to tissue compression device 10, in other examples, the method of FIG. 6 may be used with tissue compression device 90 or another tissue compression device including a flexible backing adjustably mechanically connected to a base and an expandable member mechanically connected to the flexible backing.

The method shown in FIG. 6 includes positioning a palmar surface of a hand of a patient over base 12 of tissue compression device 10 (142). In some examples, the hand of the patient may be positioned over first major surface 20 of base 12 while base 12 and flexible backing 14 are mechanically connected to each other, such as by sliding the hand between a space defined between base 12 and flexible backing or such as when backing 14 is connected to base 12, e.g., at one or only two attachment points (defined by base attachment structures 24). In other examples, the hand of the patient may be positioned on first major surface 20 of base 12 while flexible backing 14 is mechanically separated from base 12, and, after the hand is positioned on first major surface 20, flexible backing 14 may be mechanically connected to base 12.

The method of FIG. 6 also includes positioning expandable member 16 over a snuffbox of the hand of the patient (144). In some examples, expandable member 16 is mechanically connected to flexible backing 14, such that positioning expandable member 16 over the snuffbox may include tightening flexible backing 14 over the dorsal surface of the hand of the patient while the palmar surface is engaged with first major surface 20 of base 12. Depending on the anatomy of the patient, a user may also adjust the position of expandable member 16 relative to the hand of the patient, such as by repositioning flexible backing 14 relative to base 12 using the base attachment structure 24 and the backing attachment structures 34 (e.g., tightening and loosening as needed to move expandable member 16 relative to base 12). In some examples, expandable member 16 is movable relative to backing 14, and a user may detach expandable member 16 from backing 14 and then subsequently reattaching expandable member 16 to backing 14 at a different location, thereby enabling a user to adjust the position of expandable member 16 relative to base 12 and the hand of the patient.

The method of FIG. 6 also includes inflating expandable member 16 to apply pressure to tissue at the snuffbox (146). For example, expandable member 16 includes bladder 36 such that inflating expandable member 16 includes inflating bladder 36 to cause patent hemostasis of a vascular access site at the snuffbox. In some examples, base 12 includes a substantially rigid thermoplastic or a substantially rigid thermoset plastic, and flexible backing 14 includes a substantially inextensible material, such that when tissue compression device 10 is retained on the hand of the patient, the hand is constrained between the substantially rigid base 12 and flexible backing 14 and increasing pressure in expandable member 16 results in increasing pressure on tissue at the snuffbox of the hand of the patient, rather than resulting in elongation or stretching of flexible backing 14.

In examples in which expandable member 16 includes a transparent polymer, the method may include, after inflating expandable member 16, visually verifying patent hemostasis. In this way, the method may enable a clinician to use tissue compression device 10 to achieve patent hemostasis of an access site at the snuffbox of the hand of the patient.

Various examples have been described. Any combination of the described systems, devices, operations, or functions is contemplated. These and other examples are within the scope of the following claims.

What is claimed is:

1. A tissue compression device comprising:
   a base comprising:
     a major surface configured to engage a palmar surface of a hand of a patient; and
     a plurality of base attachment structures extending from the major surface;
   a flexible backing adjustably mechanically connected to the plurality of base attachment structures; and
   an expandable member mechanically connected to the flexible backing, wherein the expandable member is configured to be positioned over a snuffbox of the hand of the patient when the palmar surface of the hand is engaged with the major surface of the base, and wherein the expandable member is configured to apply pressure to tissue at the snuffbox.

2. The tissue compression device of claim 1, wherein the expandable member comprises a bladder configured to inflate to at least a pressure to cause patent hemostasis of a vascular access site at the snuffbox.

3. The tissue compression device of claim 1, wherein the expandable member comprises a transparent polymer.

4. The tissue compression device of claim 1, wherein the flexible backing comprises a plurality of backing attachment structures, and wherein each respective backing attachment structure of the plurality of backing attachment structures is configured to adjustably secure the flexible backing to a respective base attachment structure of the plurality of base attachment structures.

5. The tissue compression device of claim 1, wherein at least one base attachment structure of the plurality of base attachment structures is continuous with the major surface.

6. The tissue compression device of claim 1, wherein at least one base attachment structure of the plurality of base attachment structures is physically separate from and attached to the major surface.

7. The tissue compression device of claim 1, wherein at least one base attachment structure of the plurality of base attachment structures extends away from the major surface in a direction parallel to or transverse to the major surface.

8. The tissue compression device of claim 1, wherein the flexible backing comprises a substantially inextensible material.

9. The tissue compression device of claim 1, wherein at least one of the base or the flexible backing is configured to engage a left hand of the patient, a right hand of the patient, or both the left hand and right hand of the patient.

10. The tissue compression device of claim 1, wherein the base comprises a substantially rigid thermoplastic or a substantially rigid thermoset plastic.

11. The tissue compression device of claim 1, wherein the base comprises one or more support structures configured to reduce a range of motion of a digit of the hand or a portion of a wrist of the patient when the palmar surface of the hand is engaged with the major surface of the base.

12. The tissue compression device of claim 1, wherein the base is configured to position the hand of the patient in a predetermined configuration when the palmar surface of the hand is engaged with the major surface of the base.

13. The tissue compression device of claim 12, wherein the predetermined configuration is a grasped position.

14. The tissue compression device of claim 1, wherein the base comprises a pad configured to engage the palmar surface of the hand of the patient to position the hand of the patient in a predetermined configuration when the palmar surface of the hand is engaged with the major surface.

15. The tissue compression device of claim 1, wherein the expandable member is configured to be detached and subsequently reattached to the flexible backing.

16. A tissue compression device comprising:
   a base comprising a substantially rigid material, wherein the base comprises:
     a major surface configured to engage a palmar surface of a hand of a patient to position the hand of the patient in a predetermined configuration; and
     a plurality of base attachment structures extending from the major surface; a flexible backing comprising a substantially inextensible material, the flexible backing being adjustably mechanically connected to the base via the plurality of base attachment structures; and
   an expandable member mechanically connected to the flexible backing, wherein the expandable member is configured to be positioned over a snuffbox of a hand of a patient when the palmar surface of the hand is engaged with the major surface of the base, and wherein the expandable member is configured to inflate to apply pressure to selected tissue at the snuffbox.

17. The tissue compression device of claim 16, wherein, when the palmar surface of the hand is engaged with the major surface of the base, the predetermined configuration is a grasped position.

18. The tissue compression device of claim 16, wherein the expandable member is configured to be detached and subsequently reattached to the flexible backing.

19. A method comprising:
   mechanically connecting a flexible backing of a tissue compression device to a first base attachment structure of a plurality of base attachment structures extending from a major surface of a base of the tissue compression device, wherein the major surface is configured to engage a palmar surface of a hand of a patient; and
   mechanically connecting the flexible backing to a second base attachment structure of the plurality of base attachment structures,
   wherein the flexible backing is configured to be adjustably mechanically connected to the base, wherein the tissue compression device further comprises an expandable member mechanically connected to the flexible backing, wherein the expandable member is configured to be positioned over a snuffbox of the hand of the patient when the palmar surface of the hand is engaged with the major surface of the base, and wherein the expandable member is configured to apply pressure to selected tissue at the snuffbox.

20. The method of claim 19, further comprising positioning the palmar surface of the hand of the patient on the major surface of the base.

21. The method of claim 20, further comprising, after positioning the palmar surface of the hand of the patient on the major surface of the base, inflating the expandable member to cause patent hemostasis of a vascular access site at the snuffbox.

22. The method of claim 20, further comprising, after positioning the palmar surface of the hand of the patient on the major surface of the base, adjusting a position of the expandable member relative to the hand of the patient.

23. The method of claim 19, wherein the flexible backing comprises a plurality of backing attachment structures, wherein mechanically connecting the flexible backing to the first base attachment structure comprises adjustably mechanically connecting a first backing attachment structure of the plurality of backing attachment structures to the first base attachment structure of the plurality of base attachment structures, and wherein mechanically connecting the flexible backing to the second base attachment structure comprises adjustably mechanically connecting a second backing attachment structure of the plurality of backing attachment structures to the second base attachment structure of the plurality of base attachment structures.

\* \* \* \* \*